United States Patent
Ebert et al.

(10) Patent No.: US 11,906,497 B2
(45) Date of Patent: *Feb. 20, 2024

(54) RAPID BACTERIA TEST

(71) Applicant: Swiss Analyze Bacteria AG, Tägerwilen (CH)

(72) Inventors: Dieter Ebert, Gottlieben (CH); Mathias Reichl, Kehlheim (DE); Werner Lubitz, Kritzendorf (AT)

(73) Assignee: Swiss Analyze Bacteria AG, Tagerwilen (CH)

( * ) Notice: Subject to any disclaimer, the term of this patent is extended or adjusted under 35 U.S.C. 154(b) by 246 days.

This patent is subject to a terminal disclaimer.

(21) Appl. No.: 17/034,800

(22) Filed: Sep. 28, 2020

(65) Prior Publication Data

US 2021/0018483 A1 Jan. 21, 2021

Related U.S. Application Data

(62) Division of application No. 15/753,303, filed as application No. PCT/EP2016/069526 on Aug. 17, 2016, now Pat. No. 10,823,719.

(30) Foreign Application Priority Data

Aug. 17, 2015 (EP) .................................... 15181240

(51) Int. Cl.
| | | |
|---|---|---|
| *C12Q 1/00* | (2006.01) | |
| *G01N 33/18* | (2006.01) | |
| *G01N 33/537* | (2006.01) | |
| *G01N 33/569* | (2006.01) | |
| *G01N 33/58* | (2006.01) | |
| *G01N 21/03* | (2006.01) | |
| *G01N 21/65* | (2006.01) | |

(52) U.S. Cl.
CPC ....... *G01N 33/1826* (2013.01); *G01N 33/537* (2013.01); *G01N 33/56911* (2013.01); *G01N 33/582* (2013.01); *G01N 21/03* (2013.01); *G01N 21/65* (2013.01); *G01N 2333/195* (2013.01)

(58) Field of Classification Search
CPC ................................................. G01N 33/1826
See application file for complete search history.

(56) References Cited

U.S. PATENT DOCUMENTS

| | | | | |
|---|---|---|---|---|
| 7,608,399 | B2 * | 10/2009 | Reed | .................... C12Q 1/6851 |
| | | | | 435/6.16 |
| 7,880,876 | B2 * | 2/2011 | Zhao | ........................ B82Y 5/00 |
| | | | | 436/171 |
| 9,828,625 | B2 | 11/2017 | Koeris et al. | |
| 2001/0006783 | A1 | 7/2001 | Nogami | |
| 2014/0371106 | A1 * | 12/2014 | Hales | ........................ H01S 3/14 |
| | | | | 372/39 |

FOREIGN PATENT DOCUMENTS

| | | |
|---|---|---|
| CN | 1231701 A | 10/1999 |
| CN | 105531382 A | 4/2016 |
| EP | 0 496 345 A1 | 7/1992 |
| EP | 1 277 505 A1 | 1/2003 |

OTHER PUBLICATIONS

Reidt et al. (Journal of Rapid Methods and Automation in Microbiology vol. 16, No. 4 pp. 337-350, Dec. 2008) (Year: 2008).*
"Mikrobiologischer Trinkwassertest in weniger als einer Stunde", Optik & Photonik, Apr. 2009, No. 1, pp. 28-31.
Reidt et al., "Reproducible Filtration of Bacteria with Micromechanical Filters", Journal of Rapid Methods & Automation in Microbiology, 16, (2008), pp. 337-350.
Rompre et al., "Detection and enumeration of coliforms in drinking water: current methods and emerging approaches", Journal of Microbiological Methods, 49, (2002), pp. 31-54.
Galikowska et al., "Specific detection of *Salmonella enterica* and *Escherichia coli* strains by using ELISA with bacteriophages as recognition agents", Eur J Clin Microbiol Infect Dis, (2011) 30: 1067-1073.
Office Action issued in the parallel Chinese Application No. C 201680058074.8 dated Dec. 30, 2019 with an English translation, 16 pages.
Ulrich Reidt et al. (Journal of Rapid Methods and Automation in Microbiology vol. 16, No. 4 pp. 337-350, Dec. 2008). (Year: 2008).

* cited by examiner

*Primary Examiner* — Albert M Navarro
(74) *Attorney, Agent, or Firm* — Rothwell, Figg, Ernst & Manbeck, P.C.

(57) ABSTRACT

The invention relates to methods and devices for quantitative determination of bacteria.

13 Claims, 3 Drawing Sheets

RAPID BACTERIA TEST

CROSS REFERENCE TO RELATED APPLICATION

Figure 1:
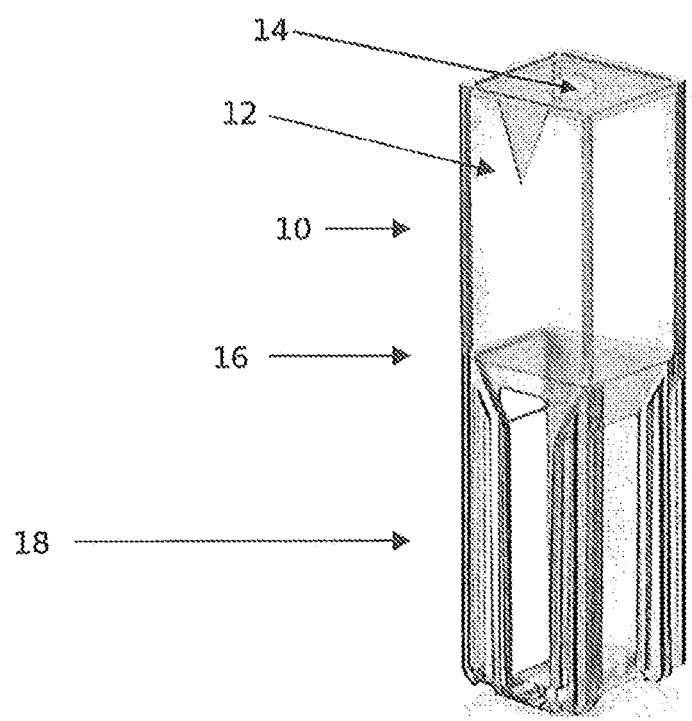

This application is a divisional of U.S. Ser. No. 15/753,303 filed Feb. 17, 2019, which is a 35 U.S.C. 371 National Phase Entry Application from PCT/EP2016/069526, filed Aug. 17, 2016, which claims the benefit of European Patent Application No. 15181240.1 filed on Aug. 17, 2015, the disclosures of which are incorporated herein in their entirety by reference.

DESCRIPTION

The invention relates to a method and to a device for quantitatively determining bacteria.

*Legionella* are gram-negative bacteria that find their optimum conditions for multiplication in water in a temperature range of from 25 to 50° C. They can be found in systems for generating and distributing hot water, in swimming pools, air washers for air-conditioning units, cooling towers, water tanks and water pipes that have long downtimes. Inhaling water containing *Legionella* in the form of an aerosol, e.g. when showering, by air-conditioning units, as a result of sprinklers or in Jacuzzis, can lead to an infection in humans that can cause a dangerous, in many cases fatal, illness known as Legionnaires' disease.

The German Drinking Water Ordinance therefore stipulates a duty to regularly test for *Legionella* which affects owners of drinking water installations comprising large-scale plants for heating drinking water, from which water is dispensed and is atomised, e.g. in showers.

This regulation is applicable to hospitals, schools, nurseries, hotels and care homes, inter alia. These establishments have a duty to test for *Legionella* once a year. Recently, owners or landlords of blocks of flats, housing associations and property management firms also have to carry out corresponding tests three times a year.

The Drinking Water Ordinance establishes a technical action value of 100 colony-forming units (CFU) per 100 ml for *Legionella*. If a test shows that this value has been exceeded, the relevant health department must be informed immediately.

Within the context of the duty to carry out a test, the analytics is carried out by means of conventional microbiological detection methods. The drinking water samples to be tested are divided up in the laboratory and tested in two parallel batches according to ISO 11731 (1998) and DIN EN ISO 11731-2 (2008). One part of the initial sample is applied directly to petri dishes containing agar medium, and another part of the sample is applied to petri dishes containing agar medium following filtration. The agar plates from both batches are incubated in an incubator for 10 days at a constant temperature of 36±2° C. Colonies of *Legionella* that grow during incubation are then counted and evaluated. The quantitative result is given in "colony-forming units" (CFU) based on 100 ml of a sample.

In order to confirm the presence of characteristic *Legionella* colonies, at least five colonies are subcultivated at the same time on both a cysteine-containing medium and a cysteine-free medium for at least two days. Since the amino acid cysteine is essential for *Legionella*, legionella is considered to be detected if the colony grows on the cysteine-containing medium but not on the cysteine-free medium.

The above-mentioned analytics is disadvantageous in that the microbiological detection method is costly and time-consuming. The method is also disadvantageous in that the results obtained thereby have a degree of inaccuracy of between approximately 15 and 35%.

The problem addressed by the present invention is therefore to provide an improved method for quantitatively determining *Legionella* and also other bacteria, in which at least some of the disadvantages of the prior art can be avoided. In particular, the method is intended to allow for considerably faster determination together with a high degree of accuracy.

In order to solve this problem, novel methods and devices for quantitatively detecting bacteria are provided. The invention relates to measuring the labelled bacteria, wherein the measurement signal obtained is correlated with the total number of bacteria present in the sample. The bacteria can be detected by means of luminescence radiation, fluorescence radiation or Raman radiation, for example.

A first aspect of the invention relates to a method for quantitatively determining bacteria in a sample, comprising the steps of:
 (a) incubating the sample to be tested together with a labelling reagent, preferably selected from a fluorescent labelling reagent, a luminescent labelling reagent and a Raman labelling reagent, which can bind to the bacteria to be determined,
 (b) removing labelling reagent that has not bound to the bacteria from the bacteria by means of a membrane that is impermeable to the bacteria to be determined and is permeable to the labelling reagent, the bacteria to be determined being collected on the membrane,
 (c) determining the labelling reagent bound to the bacteria collected, preferably by means of fluorescence measurement, luminescence measurement and/or Raman measurement, and
 (d) quantitatively evaluating the measurement signal from step (c).

The method according to the invention allows for rapid and quantitative determination of bacteria in a sample. Said method can be carried out directly after the sample has been taken and without previous cultivation of the bacteria to be determined. The incubation time required for the labelling reagent to bind to the bacteria is preferably from one second to a maximum of five minutes, particularly preferably up to a maximum of 2.5 minutes. As a result, an overall measuring time of less than ten minutes, preferably less than five minutes, can be achieved.

The method is preferably used for quantitatively determining *Legionella*. However, other bacteria, in particular human pathogenic bacteria such as *Salmonella, Listeria*, coliform bacteria such as *E. coli*, for example EHEC, or hospital germs such as MRSA, can also be determined. The sample in which the bacteria are determined can be a swipe sample or water sample as well as a biological sample, for example a food sample from meat, dairy or egg products, or a bodily fluid such as blood, plasma, serum, urine, etc.

The determination of the bacteria using the method according to the invention is carried out by using a labelling reagent that can bind to the bacteria to be determined and by measuring a signal originating from the labelling reagent bound to the bacteria. The determination can, for example, be carried out by means of luminescence measurement, fluorescence measurement and/or by measuring Raman radiation, for example by means of surface-enhanced Raman spectroscopy (SERS). In this case, a labelling reagent, preferably a fluorescent, luminescent or Raman-active labelling reagent, which can bind to the bacteria to be determined is used and is selective with regard to the bacteria to be determined, i.e. recognises a structure on or in the bacteria to be determined that is not present in other constituents of the sample. For example, the labelling reagent can be selected from labelled nucleic acid probes, antibodies, bacteriophages and combinations thereof. The labelling reagent is preferably a labelled bacteriophage.

In one embodiment, a fluorescent or luminescent labelling reagent can be used, which emits fluorescence or luminescence radiation in the range of from 200 nm to 10 µm, in particular from 200 nm to 2 µm, for example. Emission wavelengths are particularly preferably in the range of from 1300 to 1500 nm.

Fluorescence-labelled or luminescence-labelled nucleic acid probes, which are used for hybridisation with complementary bacterial nucleic acid sequences, are known in principle and are used for fluorescence in situ hybridisation (FISH technique), for example. The nucleic acid probes are usually probes based on deoxyribonucleotide analogues and/or nucleic acid analogues, e.g. LNA building blocks. They can, for example, be directed towards ribosomal RNA and/or DNA sequences that are specific to the bacterium to be detected.

Labelled antibodies, for example fluorescence-labelled or luminescence-labelled antibodies, i.e. polyclonal or monoclonal antibodies and antibody fragments or derivatives that are directed towards an antigen that is specific to the bacterium to be detected, for example an antigen present on the surface of the bacteria, are also known.

In another particularly preferred embodiment, the labelling reagent can be a bacteriophage, which bears a label, for example a fluorescence or luminescence label, and detects specific surface structures on the bacterium to be determined. Bacteriophages of *Legionella* are described by Lammetyn (Microb. Ecol. 56 (2000), 191-197), for example. Bacteriophages of *Salmonella* are described by Atterbury et al. (Appl. Environ. Microbiol. 73 (2007), 4543-4549), Wichard et al. (J. Food Prot 2 (2003), 178-340) or deLappe et al. (J. Med. Microbiol. 58 (2009)), for example. Bacteriophages of *Listeria* are described by Klumpp & Loessner (www.Ncbi.Nlm.nih.gov>PMC3827098), for example. Bacteriophages for MRSA are described by Sahin et al. (Mikrobiol. Bul. 47 (2013), 27-34), for example. Bacteriophages of *E. coli*, for example T phages, lambda phages or other phages, are described by Sambrook et al. (Molecular Cloning, A Laboratory Manual).

For the method according to the invention, labelled bacteriophages, for example fluorescence-labelled or luminescence-labelled bacteriophages, are preferably used in excess with respect to the bacteria to be detected. Approximately $10^7$ to $10^9$ phages can be used per batch. Under these conditions, every bacteria cell is usually found to be covered in approximately 50 to 400 phages, in particular approximately 50 to 250 or 50 to 150 phages. An *E. coli* bacteria cell can be covered in approximately 70 phages, for example.

In another preferred embodiment, a labelling reagent that can be detected by Raman spectroscopy can be used, for example a labelling reagent that contains a surface-enhanced Raman-spectroscopically active particle. Said labelling reagent preferably comprises a metal particle, for example a gold or silver particle and/or a Raman reporter molecule, which is bound to a probe that can bind to the bacteria to be detected. The Raman reporter molecule can be selected from an isothiocyanate dye or a multi-sulfur fluorescence dye, for example.

As described above, the probe can be selected from nucleic acids, antibodies and bacteriophages, which selectively bind to the bacteria to be determined.

The fluorescence or luminescence groups of the labelling reagent can be selected from any known organic or inorganic fluorescence or luminescence dyes, which are preferably covalently bonded to the labelling reagent. Suitable fluorescence groups are fluorescence dyes, for example fluoresceines, rhodamines, oxazines or phycoerythrins, fluorescent proteins such as GFP or variants thereof, and fluorescent quantum dots. Suitable detection groups for surface-enhanced Raman spectroscopy (SERS) are substances that comprise one or more isothiocyanate groups and/or sulfur atoms.

The bacteria to be detected are incubated together with the labelling reagent in a reaction chamber. For this purpose, the sample to be tested is introduced into the reaction chamber. The labelling reagent can be brought into contact with the sample either before or after the introduction into the first chamber. The first chamber preferably contains a store comprising a predetermined amount of labelling reagent that can be present in liquid or dry form. The labelling reagent is preferably in dry form and following contact with the sample liquid in reconstitutable form. The first chamber, in which the bacteria to be determined are incubated together with the labelling reagent, is delimited on at least one side by means of a membrane. Alternatively, the sample to which the labelling reagent has been added can be passed out of the incubation chamber and into an additional chamber, which is delimited by a membrane. Said membrane is impermeable to the bacteria to be determined but permeable to the labelling reagent, i.e. to a labelling reagent that is not bound to bacteria. Said membrane has a pore diameter of approximately 0.5 to 3 µm, for example, for example 1 to 2 µm. Suitable membranes, for example made of plastics materials such as nylon, are known.

In a preferred embodiment, a measuring cell is used in the determination method according to the invention, which cell contains at least two chambers and a membrane arranged between the chambers, which membrane is impermeable to the bacteria to be determined and is permeable to labelling reagent that is not bound to the bacteria to be determined. For example, the measuring cell can comprise a first chamber for the incubation and a second chamber for receiving separated sample constituents and excess label, which chambers are connected by means of a membrane, as described above.

Once the incubation procedure has finished, labelling reagent that is not bound to the bacteria is removed through the membrane and the bacteria to be determined are collected on the membrane. This step can be carried out by applying a vacuum to the membrane so that sample liquid that is in contact with the membrane and non-bound labelling reagent passes through the membrane and the bacteria are collected on the membrane. Alternatively, sample liquid and non-bound labelling reagent can also be removed by centrifugation. The sample liquid separated from the bacteria and the non-bound labelling reagent are preferably passed into a second chamber located behind the membrane.

The labelling reagent and the sample to be tested can be homogeneously mixed before and/or during the incubation procedure. A vibratory element that is optionally integrated in the measuring device can be provided for this purpose. Following incubation, the labelled bacteria can optionally be washed one or more times.

The first chamber provided for the incubation procedure is designed such that it can receive a sample volume that contains a sufficient amount of bacteria for a quantitative determination. The reaction chamber is usually intended for a sample volume of 0.5 ml or greater, for example 1 to 100 ml, preferably 5 to 50 ml. A volume of approximately 10 ml is particularly preferable.

The method according to the invention relates to a determination of the labelling reagent bound to the bacteria collected by means of measuring radiation, for example fluorescence radiation, luminescence radiation and/or Raman radiation, which is characteristic of the label group. For this purpose, excitation light from a light source is shone onto the bacteria collected and the fluorescence radiation, luminescence radiation and/or Raman radiation emitted by the labelling reagent located on the bacteria is measured. In a preferred embodiment, the measurement is carried out by the bacteria collected being directly tested on the membrane once the sample liquid and the excess labelling reagent have been removed and optionally after one or more washing steps.

A laser, for example a quantum cascade laser, is preferably used as the light source. This laser is connected to a suitable optical system in order to make it possible to irradiate the bacteria collected, preferably to areally irradiate the bacteria collected, preferably to areally irradiate the bacteria collected on the membrane. The laser system can be coupled into the reaction chamber by means of optically transparent fibres, for example glass fibres.

In order to detect fluorescence or luminescence, a UV-range multimode or single-mode laser diode, for example having an irradiation wavelength of from 350 to 420 nm, can be used as the laser. An irradiation wavelength of 365 nm and 405 nm, which can be achieved by using commercially available standard laser diodes, is preferable. In order to detect Raman radiation, a laser having a suitable irradiation wavelength in the UV, VIS or near-infrared range can also be used.

The labelling reagent bound to the bacteria can be determined by means of fluorescence spectroscopy, preferably by means of fluorescence correlation spectroscopy and/or by Raman spectroscopy. In this case, the excitation light originating from the light source is focussed into the sample by means of a suitable confocal optical system, in order to generate an excitation volume in which the bacteria to be determined are located.

The radiation emitted by the labelling reagent bound to the bacteria, for example fluorescence radiation, luminescence radiation and/or Raman radiation, is measured using a photodetector. The photodetector can, for example, be an avalanche photodiode or an EMCCD camera. A spectrometer is preferably used as the photodetector, which spectrometer makes it possible to spectrally resolve the emitted light over a range of at least 50 nm, at least 100 nm and up to 200 or 250 nm. A photodetector, for example a spectrometer, having a measuring range of between 200 and 2000 nm is preferably used. The optical resolution of the spectrometer is between 0.35 and 1 nm, preferably approximately 0.6 to 0.9 nm.

In one embodiment, the labelled bacteria are determined by surface-enhanced Raman spectroscopy (SERS). The method is based on the excitation of a Raman reporter molecule by means of monochromatic laser light, whereby a specific Raman spectrum is emitted. The signal is amplified by the interaction between the Raman reporter molecule and a metal nanoparticle to which it is bound. Preferred metal nanoparticles consist of a noble metal such as silver or gold and can have different structures and sizes (Wang et al., Chem. Rev. 2013, 113, 1391-1428, EP 2 134 642 B1).

The measurement signal obtained in the photodetector is quantitatively evaluated. This gives the number of bacteria present in the sample to be tested, which correlates with the measured fluorescence radiation, luminescence radiation and/or Raman radiation, as a result. The number of bacteria measured corresponds to a specific value of colony-forming units (CFU) per sample volume.

The number of bacteria determined on the basis of the measurement signal can be sorted into one or more categories using threshold values. These threshold values correlate with a fluorescence intensity specific to the particular method. If *Legionella* are detected, a first threshold value can be set, for example, which corresponds to 100 CFU per 100 ml. If the number of bacteria determined exceeds this value, measures must be taken to control the *Legionella* in the corresponding water system. 10,000 CFU per 100 ml can be set as another threshold value. If the number of bacteria determined exceeds this value, emergency measures must be taken accompanied by immediate closing down of the corresponding water system.

In order to assist with the quantitative evaluation, calibration, for example by using at least one reference signal that can be generated by means of a reference laser, can be carried out. Alternatively, calibration can also be carried out by using internal standards, for example fluorescent, luminescent or Raman-active particles, which bear a fluorescence label, luminescence label or Raman label that is different from the optically detectable labelling reagent.

The present invention also relates to a measuring cell for quantitatively determining bacteria, comprising
(i) a first chamber, which optionally contains a store containing a labelling reagent for the bacteria to be determined, for example bacteriophages, the labelling reagent preferably being selected from a fluorescent labelling reagent, a luminescent labelling reagent and a Raman labelling reagent,
(ii) a second chamber, and
(iii) a membrane, which is arranged between the first chamber and the second chamber, the membrane being impermeable to the bacteria to be determined and being permeable to labelling reagent that is not bound to the bacteria to be determined.

The present invention also relates to a device for quantitatively determining bacteria, comprising:
(i) a measuring cell as specified above,
(ii) means for withdrawing excess labelling reagent from the first chamber and passing it into the second chamber,
(iii) means for exciting the radiation, for example the fluorescence radiation, luminescence radiation and/or Raman radiation, of labelled bacteria that are collected on the membrane, and
(iv) means for quantitatively evaluating a measurement signal originating from the bacteria collected.

The measuring cell and the device according to the invention can be used in a method for quantitatively determining bacteria, in particular in the above-described method according to the invention. The use for quantitatively determining *Legionella* in a water sample is particularly preferred.

The invention is also intended to be explained using the following figures:

FIG. 1 shows a measuring cell, which is formed as a measuring cuvette. The measuring cell contains a reaction chamber or first chamber (10) for receiving a sample volume of for example 10 ml. A label store (12) having a predetermined amount of labelling reagent, preferably in dry form, is provided in the first chamber (10). The first chamber (10) contains an opening (14) on one side for receiving the sample. Furthermore, the first chamber (10) is connected to a second chamber (18) by means of a membrane (16). The membrane (16) is designed so as to be impermeable to bacteria present in the first chamber (10) but to be permeable to labelling reagent that is not bound to bacteria.

For the measurement, the liquid in the first chamber (10) is passed into the second chamber (18) following incubation together with the labelling reagent. Bacteria that are present in the sample and comprise labelling reagent bound thereto are deposited on the membrane (16). Labelling reagent that is not bound can pass through the membrane (16) and enters the second chamber (18), together with the liquid. The bacteria deposited on the membrane (16) can be measured in situ, without additional measures.

Figure 2:
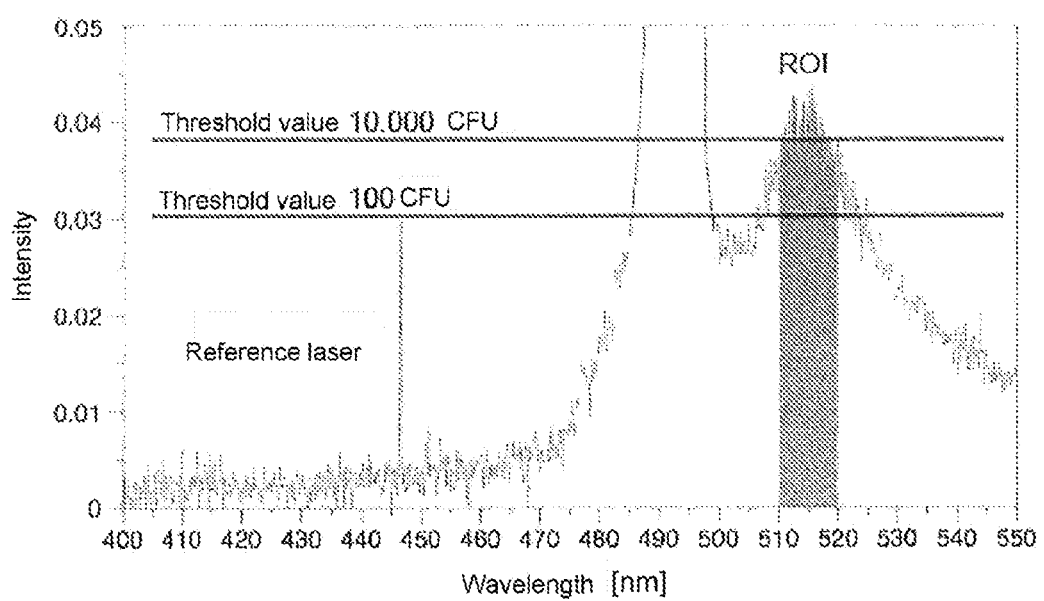

FIG. 2 shows the result of a spectral measurement on a sample that has tested positive for the bacteria to be detected, for example *E. coli* or *Legionella*. The measurement signal is recorded by a spectrometer, the measuring range of which is preferably between 350 and 550 nm. The optical resolution of the spectrometer is preferably from 0.4 to 0.1 nm. The fluorescence signal originating from the bacteria to be determined is in the range of from 510 to 520 nm (ROI). A reference laser is used to ensure that the amplitude of the spectrum has a correct reference value. The evaluation comprises establishing two threshold values for bacterial counts of 100 CFU per 100 ml and 10,000 CFU per 100 ml. In the figure, the intensity of the measuring signal exceeds the threshold value of 10,000 CFU. Thus, the sample determined is extremely contaminated.

Figure 3:
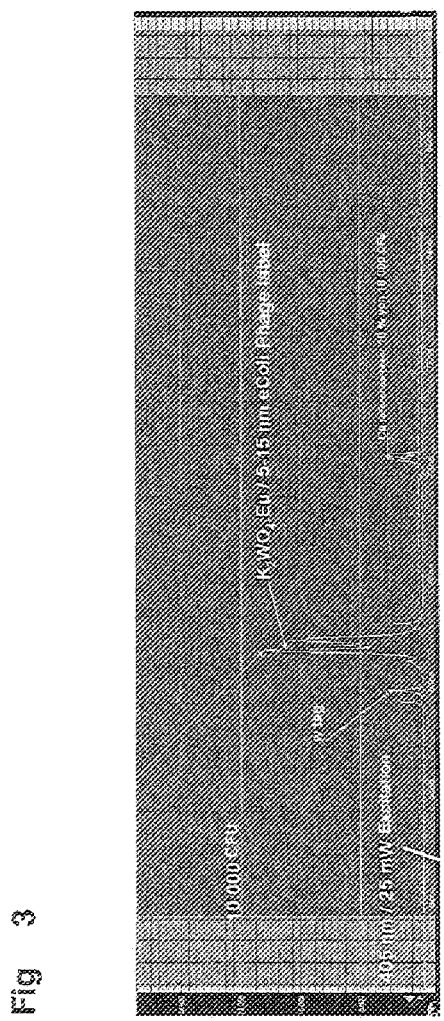

FIG. 3 shows the result of determining a sample with *E. coli* bacteria. *E. coli* phages coupled to the inorganic dye $K_2WO_4$:Eu (particle size of 5 to 15 nm) were used as the labelling reagent.

After incubation together with the labelling reagent in a reaction chamber, the bacteria contained in the sample were deposited on a membrane where they were determined. For this purpose, the membrane was homogeneously illuminated by a laser (405 nm/25 mW) and the emission radiation generated at a wavelength of from 610 to 615 nm was quantitatively determined. The quantitative conversion of the signal measured in corrected impulses into the number of colony-forming units (CFU) in the sample was possible by means of previous calibration using standard samples having a known number of *E. coli* bacteria, for example in the range between 10 and $10^9$ cells.

The peak of a Ca reference laser, which has been irradiated with an intensity corresponding to 10% of the threshold value of 10,000 CFU, can be seen at 702 nm in the spectrum.

Another signal, which is not used for quantitatively determining the bacteria, from the wolfram label contained in the dye can be detected in the range between 590 and 600 nm.

The determination of the sample shown in FIG. 3 resulted in a signal that corresponds to a bacterial count of 9,030 CFU. This bacterial count could be verified by using FACS for verification.

The invention claimed is:

1. A method for quantitatively determining bacteria in a sample, comprising the steps of:
   (a) incubating the sample to be tested together with a labelling reagent that can bind to the bacteria to be determined in a measuring cell comprising a first and a second chamber, wherein the labelling reagent is a labelled bacteriophage, wherein said sample is incubated in the first chamber of said measuring cell,
   (b) removing labelling reagent that has not bound to the bacteria from the bacteria by means of a membrane arranged between the first and second chamber, wherein said membrane is impermeable to the bacteria to be determined and is permeable to the labelling reagent that is not bound to the bacteria to be determined, wherein the bacteria to be determined are collected on the membrane and said labelling reagent that has not bound to the bacteria is moved into said second chamber,
   (c) detecting the labelling reagent bound to the bacteria collected on said membrane, and
   (d) quantitatively evaluating the measurement signal from step (c), wherein the quantitative evaluation of the measurement signal comprises a calibration by using an internal standard.

2. The method according to claim 1, wherein the bacteria are selected from the group consisting of legionella, salmonella, listeria, coliform germs, and hospital germs.

3. The method according to claim 1, wherein said membrane has a pore diameter of approximately 0.5 to 3 µm.

4. The method according to claim 1, wherein the labelling reagent and the sample to be tested are mixed before and/or during the incubation procedure in step (a).

5. The method according to claim 1, wherein the labelling reagent bound to the bacteria is detected in step (c) using a laser with a confocal optic as the light source.

6. The method according to claim 5, wherein the laser is used in an integrated device together with a spectrometer so as to form a detection unit.

7. The method according to claim 1, wherein the quantitative evaluation in step (d) comprises sorting a specific number of bacteria into one or more categories on the basis of predetermined threshold values.

8. The method according to claim 1, wherein at least one reference signal is used for the quantitative evaluation in step (d).

9. The method according to claim 1, wherein the internal standard comprises fluorescent, luminescent or Raman-active particles, which bear a label that is different from said labelling regent.

10. The method according to claim 1, wherein the labelling reagent is selected from the group consisting of a fluorescence-labelled bacteriophage, a luminescence-labelled bacteriophage and a Raman-labelled bacteriophage and wherein said labelling reagent bound to the bacteria collected, is detected by means of fluorescence measurement, luminescence measurement and/or Raman measurement.

11. The method according to claim 2, wherein the coliform germs are *Escherichia coli*, and the hospital germs are Methicillin-resistant *Staphylococcus aureus*.

12. The method according to claim 1, wherein said first chamber contains a store for the labelling reagent.

13. The method according to claim 8, wherein said at least one reference signal is generated by a laser.

* * * * *